United States Patent
Cant et al.

(10) Patent No.: US 12,082,959 B2
(45) Date of Patent: Sep. 10, 2024

(54) METHOD FOR POSITIONING A MOBILE TOMOGRAPHY DEVICE

(71) Applicant: AGFA NV, Mortsel (BE)

(72) Inventors: Jeroen Cant, Mortsel (BE); Vincent Van Nieuwenhove, Mortsel (BE)

(73) Assignee: Agfa NV, Mortsel (BE)

( * ) Notice: Subject to any disclaimer, the term of this patent is extended or adjusted under 35 U.S.C. 154(b) by 230 days.

(21) Appl. No.: 17/875,789

(22) Filed: Jul. 28, 2022

(65) Prior Publication Data
US 2023/0032243 A1    Feb. 2, 2023

(30) Foreign Application Priority Data
Jul. 29, 2021 (EP) .................................. 21188413

(51) Int. Cl.
*A61B 6/00*    (2024.01)

(52) U.S. Cl.
CPC .......... *A61B 6/4405* (2013.01); *A61B 6/4429* (2013.01); *A61B 6/547* (2013.01)

(58) Field of Classification Search
CPC ..... A61B 6/4405; A61B 6/4429; A61B 6/547; A61B 6/025; A61B 6/4476; A61B 6/08
See application file for complete search history.

(56) References Cited

U.S. PATENT DOCUMENTS

| | | | |
|---|---|---|---|
| 9,788,810 B2* | 10/2017 | Ancar | A61B 6/547 |
| 2015/0230768 A1* | 8/2015 | Belei | A61B 6/4405 |
| | | | 378/62 |
| 2018/0092613 A1* | 4/2018 | Ancar | A61B 6/487 |
| 2020/0163635 A1 | 5/2020 | Kumar et al. | |

FOREIGN PATENT DOCUMENTS

| | | |
|---|---|---|
| EP | 2835103 A1 | 2/2015 |
| KR | 20200086466 A * | 7/2020 |

OTHER PUBLICATIONS

Zhao et al., "Mobile X-ray Tomography System with Intelligent Sensing for 3D Chest Imaging," *Medical Imaging 2021: Physics of Medical Imaging*, vol. 11595, SPIE (2021).

* cited by examiner

*Primary Examiner* — Kiho Kim
(74) *Attorney, Agent, or Firm* — Leydig, Voit & Mayer, Ltd.

(57) ABSTRACT

This invention is related to a method to adjust the starting position of an acquisition trajectory of a mobile X-ray device that is to perform a portable X-ray tomography acquisition sequence. The invention supports an operator in positioning a mobile X-ray device such that it can subsequently successfully and autonomously perform a digital tomosynthesis exam. Alternatively may an operator provide visual input on a camera image on where he desires the tomosynthesis acquisition to be performed, allowing the mobile X-ray device to adjust its initial starting position autonomously.

15 Claims, 5 Drawing Sheets

METHOD FOR POSITIONING A MOBILE TOMOGRAPHY DEVICE

CROSS-REFERENCE TO RELATED APPLICATION

Figure 1:
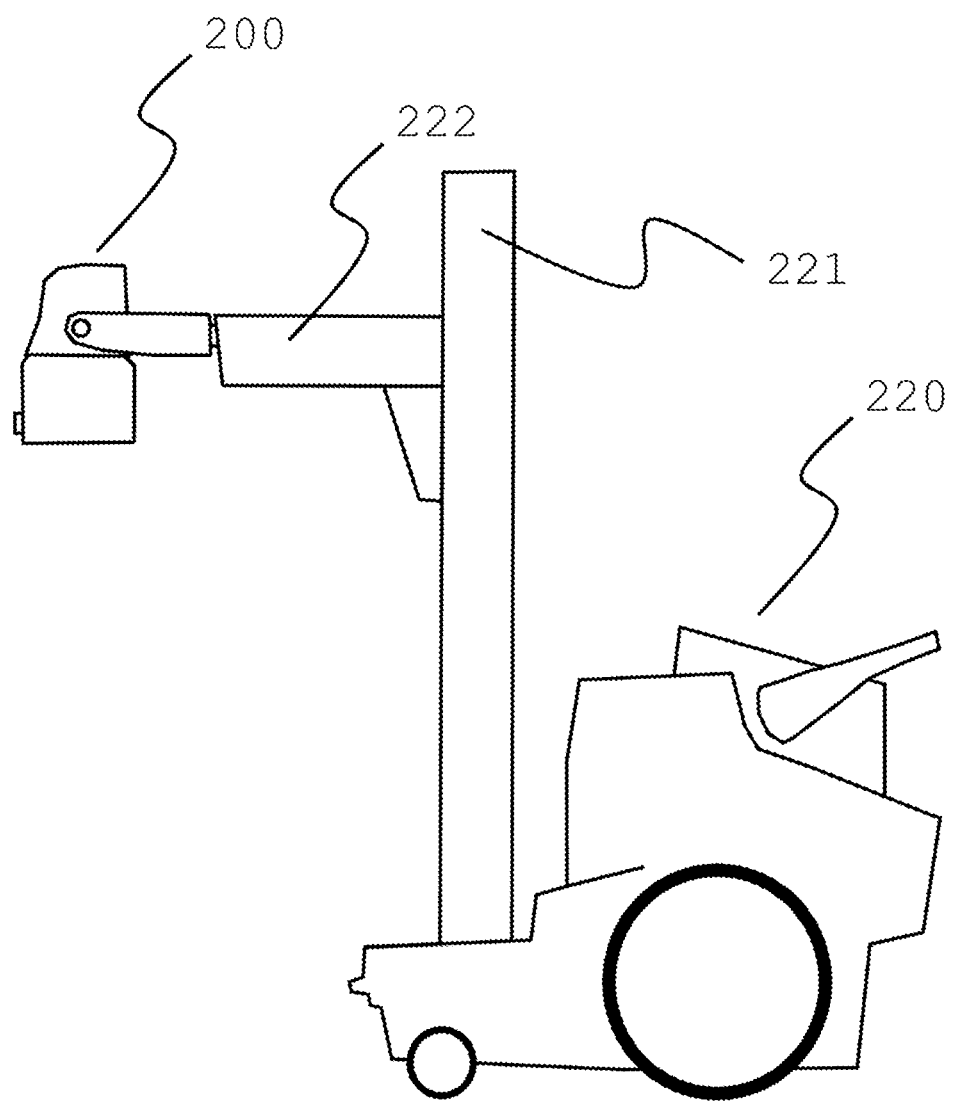

This patent application claims the priority of copending European Patent Application No. 21188413.5, filed Jul. 29, 2021, which is hereby incorporated by reference in its entirety.

TECHNICAL FIELD

The present invention relates generally to a method to accurately position an X-ray source of a mobile tomography X-ray device in preparation of an automated tomography acquisition motion sweep.

BACKGROUND OF THE INVENTION

Digital tomosynthesis or X-ray tomography is an X-ray technique that bridges the gap between traditional X-ray projection radiography and CT imaging. Digital tomosynthesis is a method for performing high-resolution limited-angle tomography at radiation dose levels comparable with projectional radiography. While X-ray projection radiography produces a 2D projection X-ray image, digital tomosynthesis produces a set of tomographic slices that become available after tomographic image reconstruction.

Chest X-ray radiography is one of the oldest radiography techniques used, and still provides today a lot of advantages such as its cost-effectiveness, the low doses involved and the high quality of the images. Nevertheless is chest X-ray radiography prone to errors relating to small structures that may be masked by other and more dense structures in the image (such as for instance ribs or other bony structures). This problem, known as "anatomical noise" can be resolved by tomosynthesis.

Portable X-ray tomography is a technique wherein a mobile X-ray device is used to provide a motion sweep of the X-ray source to acquire a sequence of radiography images, called tomography images. The set of tomography images is acquired by a digital detector onto which an X-ray source projects its X-ray beam each time under slightly different angles and at a very low doserate per image (typically 1/10th of a traditional acquisition).

The digital X-ray detector is positioned behind the object or patient that is to be imaged, and should ideally capture the sequence of images while the full surface of the detector is irradiated entirely. The moving X-ray source is mounted on a motorized arm or cart that supports the X-ray source during the tomography movement, meaning that either the cart on which the X-ray source is mounted performs a movement on the floor, or else that the X-ray source travels with a motion along a known path that is effected by a movement of a suspending device of the X-ray source.

It is a requirement for the image reconstruction that the relative position of the X-ray source in relation to the digital imaging detector is accurately known at the locations of each acquired image. In practice however, will the relative movements of the X-ray source and digital imaging detector be arranged as linear or circular movements, as this makes the accurate position tracking easier.

Tomosynthesis reconstruction algorithms are similar to CT reconstructions, in that they are based on performing an inverse Radon transform. Alternative and more preferred algorithms to apply in tomosynthesis reconstruction are iterative reconstruction algorithms such as algebraic or statistical reconstruction algorithms.

Due to partial data sampling with very few projections, approximation algorithms have to be used. Filtered back projection and iterative algorithms have both been used to reconstruct the data. Reconstruction algorithms for tomosynthesis are different from reconstruction algorithms used in conventional CT because the conventional filtered back projection algorithm requires a complete set of data. Iterative algorithms yield an improved image quality, but are computationally intensive. The reconstruction result is a stack of images that are oriented in plane or parallel with the surface of the digital X-ray detector.

While X-ray tomosynthesis is commonly applied in certain dedicated applications such as for instance mammography, multi-purpose X-ray tomography becomes more popular as a technique as it can be performed using a standard X-ray modality that however is minimally adapted to perform a tomography acquisition sequence. In practice, the modality needs to support a motion of the X-ray source (and/or the digital imaging detector) while capturing the sequence of digital images by the digital imaging detector, and this preferably in an automated way.

The motion can relatively easily be achieved in fixed X-ray installations, because the movements of many ceiling suspensions or tube cranes are intrinsically composed out of a combination of movements. A ceiling mounted X-ray tube suspension typically comprises for instance two orthogonally mounted support beams on which the X-ray tube carriage is able to float in the direction of two orthogonal axes. In order to perform e.g. a linear motion along one of the principal axes only one of the motor actuators has to be driven at a constant speed.

Achieving a linear motion under less controlled conditions, such as when performing a tomography acquisition using a mobile X-ray device, is harder to establish. The requirements of the linear motion and the constant velocity have to be achieved by a different type of electrical motor powered movement. The most obvious choice for such a motorized movement for a mobile X-ray device that can be controlled is the movement of the cart of the mobile X-ray device over the floor surface. The same motorized movement to move the mobile X-ray cart around is used in this case. As such it will be important that the floor surface is horizontal and as smooth as possible in order to make the impact of the electrical motor movement predictable. Also important is it to ensure that no obstacles can obstruct the linear movement during the acquisition phase, nor that irregularities on the floor surface may cause distortions in the acquisition geometry during the image acquisitions.

Other technical problems arise when trying to acquire tomography images with a mobile X-ray device. The alignment of the X-ray tube with the patient and the digital imaging detector is for instance not a trivial matter. A tomography acquisition requires a series of consecutive exposures taken from different angles with respect to the surface of the digital imaging detector. The series of exposures need to be programmed along an intended trajectory of the X-ray source, which may be hard to realize under all circumstances.

A typical mobile X-ray modality cart is a heavy device that is built for stability during exposure while the cart is at standstill. Because of its weight it requires some effort and force to accelerate it towards a constant velocity, which is required for a tomography acquisition. Moreover, is it hard to determine where the cart has to be positioned for a suitable starting position. Also the length of the active portion of the acquisition trajectory or path has to be determined in order to ensure that the entire region of interest is imaged, and that—at the same time—the digital imaging detector is exposed fully. This active portion of the acquisition trajectory thus has to take into account the source-to-detector distance (SID), the detector width, the size of the region of interest, and the collimator settings (determining the width and height of the exposure field).

This invention intends to overcome the aforementioned problems and will disclose how the specific hurdles characterizing the tomographic technique may be overcome using a mobile X-ray modality.

SUMMARY OF THE INVENTION

The present invention provides a method for adjusting a starting position of an acquisition trajectory of a mobile X-ray device of which said acquisition trajectory is setup in parallel to a digital imaging detector to perform a portable X-ray tomography acquisition sequence on a region of interest of an object, comprising the steps of receiving X-ray source collimator settings, positioning said mobile X-ray device by an operator in an initial starting position for said portable X-ray tomography acquisition sequence, calculating said acquisition trajectory of said mobile X-ray device during said portable X-ray tomography acquisition sequence for said initial starting position, characterized in that, the acquisition trajectory of said mobile X-ray device during said portable X-ray tomography acquisition sequence for said initial starting position is visualized for each change in position of said mobile X-ray device, said initial starting position for said acquisition trajectory is adjusted interactively by said operator by moving said mobile X-ray device, such that said a trajectory portion of said visualized acquisition trajectory is aligned with said region of interest of said patient.

In the context of this invention, a tomography acquisition or tomography sequence consists of a series of X-ray acquisitions (or projection radiographies) that meet the requirements to perform a tomosynthesis reconstruction. A tomography sequence is performed by acquiring a series of consecutive X-ray acquisitions or radiographies wherein the X-ray source has a slightly different angle with respect to the detector surface, and wherein the patient or imaged object is assumed to be immobile. In an ideal situation, the different acquisitions are performed in a stop-go manner to ensure that the entire acquisition of the detector stems from the same detector position. In real life however, this criterion does not necessarily has to be met since the actual time of an image is short relative to the continuous motion of the X-ray source. In other words, the acquisition of a full image by the detector is very short (10-20 ms) with respect to the speed of the X-ray source during the tomosynthesis sweep.

A portable X-ray tomography acquisition is a tomography acquisition, that is performed on a mobile X-ray device. It is called "portable" as it refers to its portability and flexibility in setting up the system. Such a portable X-ray tomography system involves the use of a portable digital imaging detector that is positioned behind a patient. The portable digital imaging detector is typically a wireless detector, meaning that it can operate in a wireless fashion while not being physically connected to another device. The portable imaging detector may also be connected to the imaging workstation via a cable, but this is for practical reasons not preferred.

A mobile X-ray device has to be considered as being a fully independent X-ray or radiography system that comprises all essential parts to perform a standard projection radiography image. It therefore comprises an X-ray source or X-ray tube, a high voltage generator driving the X-ray tube, a digital imaging detector, an image processing workstation and a battery pack to power all the above mentioned components. These components are typically integrated into the cart of the system which makes the device mobile, and comprises a number of wheels supporting it. The wheels may be motor driven and allow the cart to be moved around with reasonable physical effort. The cart integrates and physically supports the above mentioned essential X-ray components, and comprises mechanical components to support them (such as for instance an X-ray tube-support or arm).

An important aspect of the tomography acquisition sequence to allow a tomographic reconstruction, is that the positions of the X-ray source and the digital imaging detector at the time of each radiography acquisition are accurately known with respect to each other. Only under these circumstances can the radiography images be reconstructed into a tomographic image set. While it is not an absolute mathematical requirement, most practicable tomosynthesis reconstruction algorithms require linear movements or movements along an arc between the X-ray source and digital imaging detector, avoiding the complexity of having to integrate detailed positional information per image in the tomographic reconstruction. As a consequence of this, the tomography acquisition sequence has to be performed while ensuring that the respective positions of the X-ray source, digital imaging detector and patient can be determined or are recorded in order to be known at the time of reconstruction.

Another characterizing aspect of a tomography acquisition sequence, is that the distances between the positions of the acquired images in a sequence are ideally the same, in order to ensure a consistent reconstruction. So, in order to achieve this, it is preferred to acquire the images in an acquisition sequence while moving the X-ray source (and/or the digital imaging detector) at a constant speed when acquiring the sequence. When moving the components at a constant speed with respect to each other, it suffices that the image acquisitions are made at constant time intervals in order to obtain images that are acquired at identical distances from each other. When this criterion is met, the best reconstruction results are achieved and a consistent reconstruction quality can be achieved across the image stack.

As explained above, the most feasible way to separate the different acquisitions at a constant distance from each other on a linear path is to attempt to achieve a constant moving speed of the X-ray source with respect to the digital image detector, and then to time the acquisitions at constant intervals.

The constant speed requirement should therefore be imposed on the part of the device that moves during the image acquisition sequence. For a mobile X-ray device, this may be the cart or the beam onto which the X-ray tube is attached. Remains to be solved on how to bring this component to a constant velocity in a predictable way.

Programming an X-ray device to capture images at constant intervals is not so much of a challenge, but achieving a constant and linear motion of a mobile X-ray device over a floor surface is. The cart or trolley of a mobile X-ray device is a heavy object that exhibits a significant inertia when it is brought into motion by a force such as for instance electrically powered wheels. The mobile X-ray system, depending on its configuration in terms of engine power, transmission onto the wheels and the weight of the entire system, will require a certain ramp-up time before the desired constant speed is achieved. This ramp-up time may furthermore be influenced by differences in surface material on which the cart moves, by the slope of the surface, or by the presence of any obstacles or unevenness.

It is obvious that the ramp-up length (or run-up space) has to be accounted for when positioning the device in preparation of a programmed tomography acquisition movement of the system. This ramp-up length will require that the system will be positioned "ahead" of the active zone or acquisition phase in which the acquisition actually has to take place. Ideally the ramp-up length can be limited to the distance that the cart requires to achieve the constant velocity, in order to limit the ramp-up length to what is strictly necessary, and not to position the cart too far away from the active zone.

On a similar note will the device require a slow-down length or run-down space to come to a complete halt after the programmed acquisition run has been performed. Moreover the run-up space, run-down space and the entire acquisition path has to be clear from obstructions before a successful acquisition can be performed.

In case that the tomographic movement of the source is not performed by the cart of the mobile X-ray system, but rather by a part or a combination of telescopic parts of the tube crane, similar problems arise with the acceleration (ramp-up and ramp-down) of the X-ray source. The moving part(s) will have to allow a sufficiently long acquisition trajectory taking the accelerations into account. Since most of the telescopic positioning extensions only allow limited movement due to their construction in combination with the fact that they are seldom motorized, the desired setup to perform such tomographic acquisition sequence is by movement of the entire cart over the floor.

Another aspect of the position of the X-ray source, and more specifically the positioning of the X-ray beam, with respect to the digital imaging detector is that the X-ray beam should cover the digital X-ray detector entirely when it is travelling at the above mentioned constant speed. This implies that the collimator settings should allow the detector to be exposed/illuminated during the entire active path of the X-ray source.

When preparing a system setup for a tomographic image acquisition sequence, the difficult part for the operator is two-fold. First of all when positioning the mobile X-ray device in preparation of the execution of the programmed tomography movement, the operator has no visibility on where the actual acquisition phase of the sequence will actually commence given a certain starting position of the cart or the X-ray tube. In other words, without any further assistance, it will be virtually impossible for an operator to know or estimate where the tomographic acquisition will take place. Neither will he be able to determine whether the current starting position of the system will result in the desired acquisition of images. This is of course unacceptable as it would lead to errors, or retakes. Moreover, the positioning error will grow larger when the distance that is needed to achieve the constant velocity is larger.

In the context of the invention, the starting position of an acquisition trajectory coincides with the current position of the cart before the acquisition sequence is started. If the acquisition sequence would be started with the cart in the current position as a starting position, this would result into a certain acquisition path which can be calculated and visualized by the method and system of the invention. The visualized acquisition path can be used as an input for an operator to adjust the starting position which then has an input on the anticipated acquisition trajectory. The impact of the changed starting point can be immediately re-evaluated by the operator as the visualized acquisition path is updated immediately by the system.

For an acquisition sequence to result in a successful tomographic acquisition sequence, the relative paths of the X-ray source and the digital imaging detector have to be known accurately, and should preferably be in parallel with respect to each other in order to keep the geometries of the relative paths simple.

The second problem for the operator is that without any further assistance from the invention, he will not be able to adjust or optimize the collimation field (or exposed zone) to perform the tomographic acquisition sequence, by ensuring that the digital imaging detector is fully exposed. In other words the operator will have difficulty to determine how extensive the acquisition phase should be programmed to ensure that the desired region of interest is imaged by the system.

The invention therefore intends to support the operator to adjust the initial positioning of the cart or mobile X-ray device by providing visual guidance that is combined with the visual tools that are available to him at that moment. The position is adjusted interactively by the operator, meaning that the operator provides adjustments to the starting position based on what he observes in the visualizations of the acquisition trajectory or trajectory portion. At the very first time that the mobile X-ray device is positioned by the operator, he will have to make an estimated guess of a suitable initial starting position before the method of the invention is applied; the operator therefore has to position the system based on an estimated acquisition trajectory to align the mobile X-ray device (with the X-ray source) with the digital imaging detector.

A trajectory portion has to be understood as a well-determined part or portion of the complete acquisition trajectory that performs a certain function during the acquisition sequence. A trajectory portion may at least refer to the ramp-up phase, acquisition phase or the slow-down phase of the acquisition trajectory. Other trajectory portions may be defined. A trajectory portion of said visualized acquisition trajectory, therefore refers to a visualized trajectory portion that is part of the visualized acquisition trajectory.

The visualization of the acquisition trajectory or the trajectory portion has to be understood as the application of visual markings in for instance an acquired image by a camera that is physically associated with the X-ray source, by drawing lines on this image, or alternatively by projecting markings or lines onto the object or patient directly by an image projector that is physically associated with the X-ray source. In both instances, it is desirable that the location of the camera or projector is close to the X-ray source as both the camera and projector should ideally have the same viewing (or projection) perspective as the X-ray source. In case that there would not be close correspondence in the locations of the camera or projector with the X-ray source, corrections would have to be performed to compensate for the misalignment.

The invention is advantageous in that it resolves the difficulties with regards to the estimations that an operator needs to make to prepare and perform a tomographic acquisition sequence on a mobile X-ray device.

Specific examples and preferred embodiments are set out in the dependent claims.

BRIEF DESCRIPTION OF THE DRAWING(S)

FIG. 1 depicts a mobile X-ray device, comprising a motorized cart (220), and X-ray source or X-ray tube (200)

that is mounted on an extendible arm (222). The extendible arm is in its own turn fixed to a mount (221), around which the extendible arm can rotate. The view depicted here shows a position of the device wherein the extendible arm (222) is lined up with the body of the cart (220).

Figure 2:
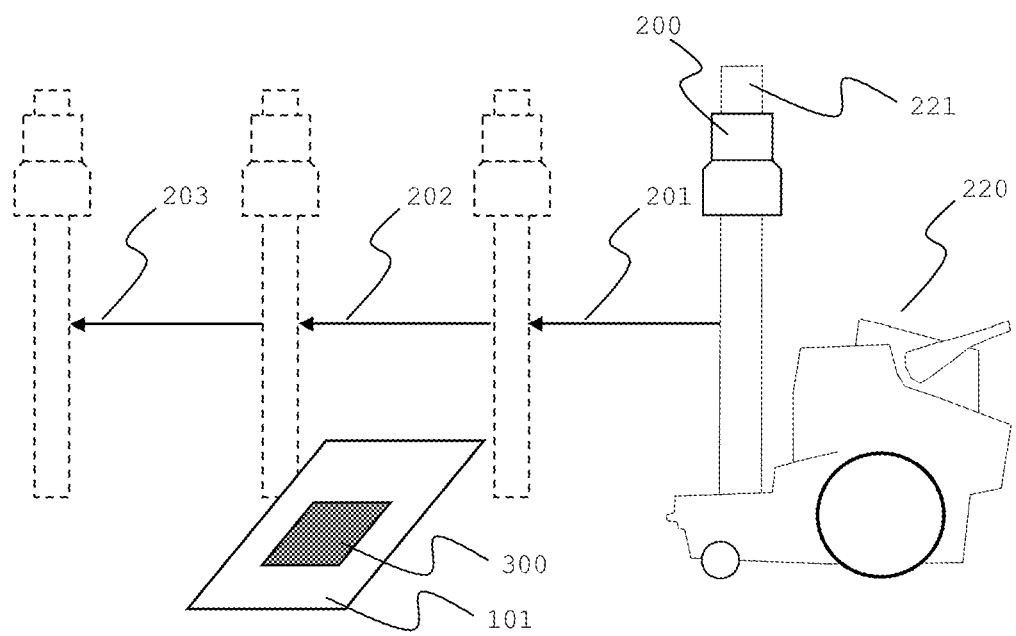

FIG. 2 depicts the same mobile X-ray device wherein the extendible arm (222) is not visible because it is oriented perpendicularly and laterally onto the side of the body of the cart (220). The X-ray tube (200) is therefore also oriented towards the viewer. The view depicts the X-ray tube (200) in front of the extendible arm (222) which is not visible because of this and which is oriented towards the viewer. The same figure shows a table top (101) of a patient positioning device that is positioned close to the mobile X-ray device. On the table top surface, a digital detector cassette (300) is shown. The X-ray tube mount (221) carries the X-ray tube (200). The X-ray tube mount (221) carrying the X-ray tube (200) is depicted multiple times, and is shown on its movement path or trajectory during a tomosynthesis acquisition or tomo sweep (201+202+203). The first trajectory portion (201) refers to the ramp-up phase of the mobile X-ray device, wherein the device ramps up from stand still to a constant velocity. The second trajectory portion (202) refers to the constant velocity portion or acquisition phase, during which the motorized cart (220) moves at a constant speed, and during which the surface of the digital imaging detector (300) is completely exposed by the X-ray source. The third trajectory portion (203) refers to the slow-down phase of the mobile X-ray device, wherein the device slows down to a complete stand-still.

Figure 3:
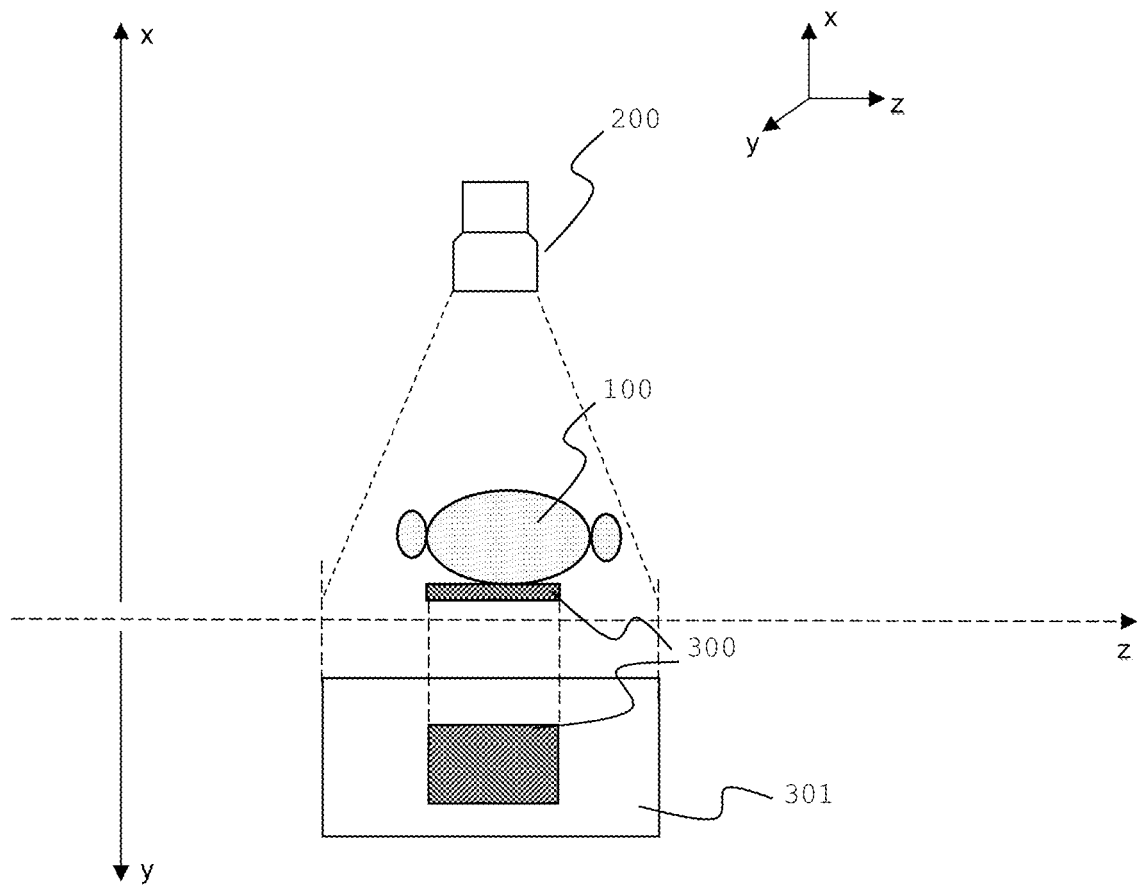

FIG. 3 depicts a dorsally positioned patient (100) in contact with a digital detector cassette (300) that is positioned at the opposite side of the patient from the X-ray tube (200). The drawing represents two orthogonal projection; above the horizontal z-axis the projection in the xz-plane is depicted and represents a lateral view of the setup. Below the z-axis, the projection in the yz-plane is depicted and represents a top-to-bottom view of the setup, showing the top surface of the digital detector cassette (300), and the collimated projection field (301) of the X-ray source (200).

Figure 4:
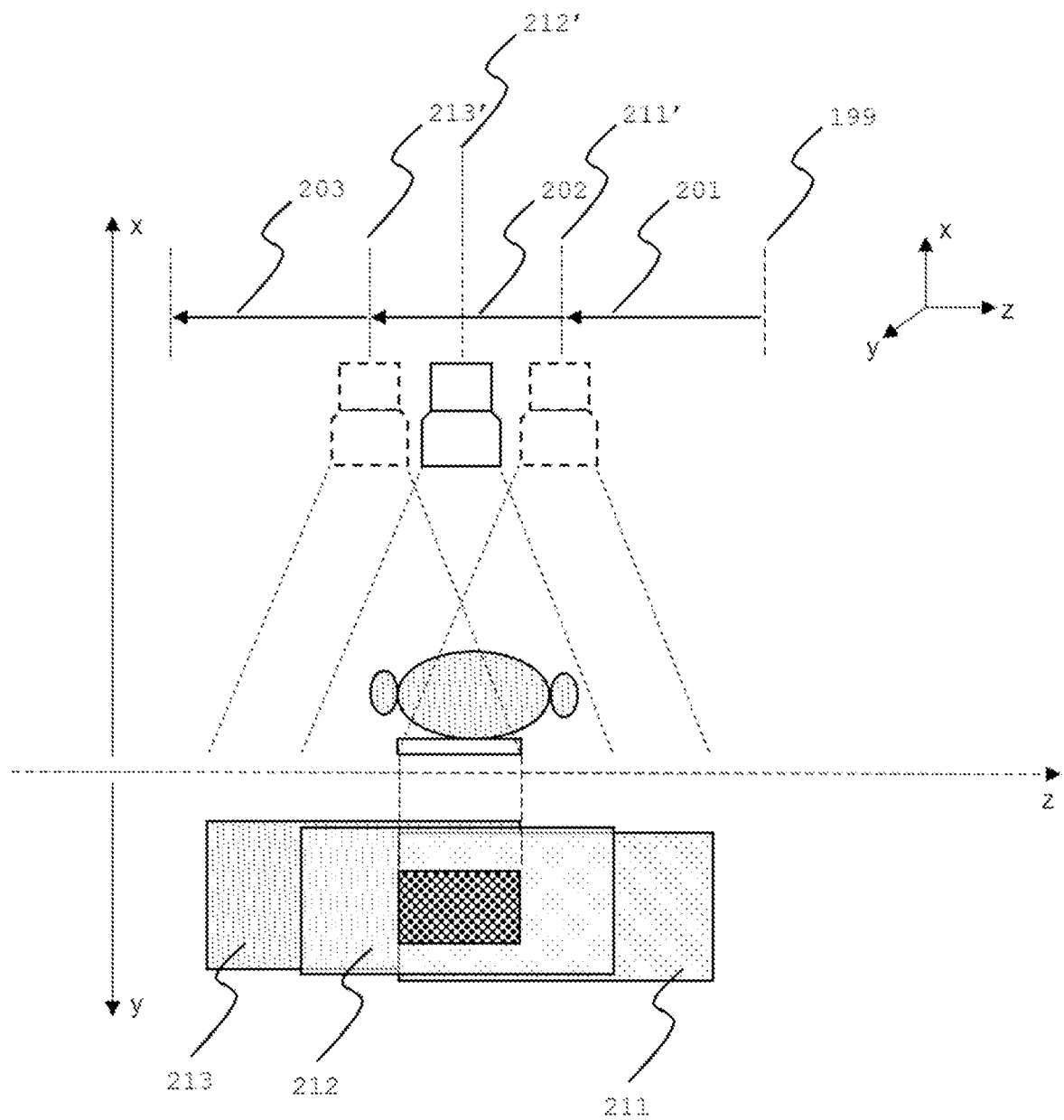

FIG. 4 shows, in the same projection as in FIG. 3, the movement path or trajectory of the X-ray tube during a tomosynthesis acquisition or tomo sweep (201+202+203). Below the z-axis, the projection in the yz-plane depicts the respective collimated projection fields (211, 212, 213) of the corresponding X-ray tube positions (211', 212', 213') together with the top surface of the digital detector cassette (300). (199) represents the starting position of the X-ray tube before the acceleration of the X-ray tube is initiated. The diagram again depicts the movement path or trajectory during the tomosynthesis acquisition, and shows the different trajectory portions (201, 202, 203) as explained above. In this diagram, it becomes clear that when the X-ray source arrives at position (211') it is the first time that the corresponding projection (211) of the projected X-ray beam completely overlaps with the surface of the digital detector cassette (300). At this position (211') the X-ray tube will also have gained the constant speed of the constant velocity portion or acquisition phase (202). It is during this acquisition phase (202) that the digital imaging detector (300) will continuously capture images at a constant acquisition frequency. The combination of the constant acquisition frequency and the constant velocity of the X-ray source, ensures that the sequence of tomographic images in the interval (202) are captured at the same distance from each other.

Figure 5:
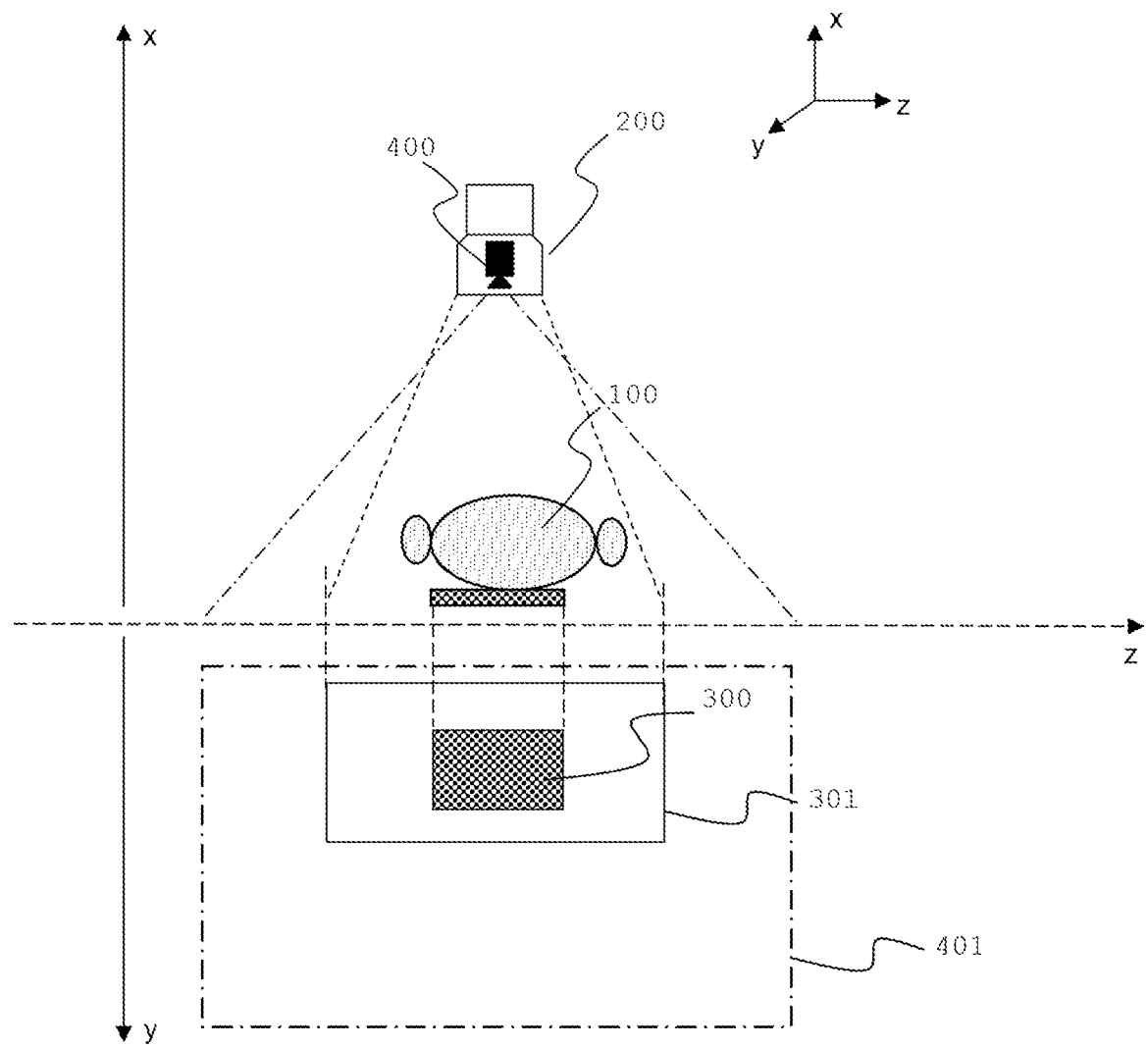

FIG. 5, in the same projection as in FIG. 3, depicts the X-ray source (200) of the tomography X-ray device to which a camera device (400) is attached. This camera device is physically attached to the collimator head of the X-ray source and is pointed in the direction as the X-ray beam itself. The viewing field (401) of the camera device at least comprises the projected field size of the X-ray beam (301) and preferably exceeds it.

Figure 6:
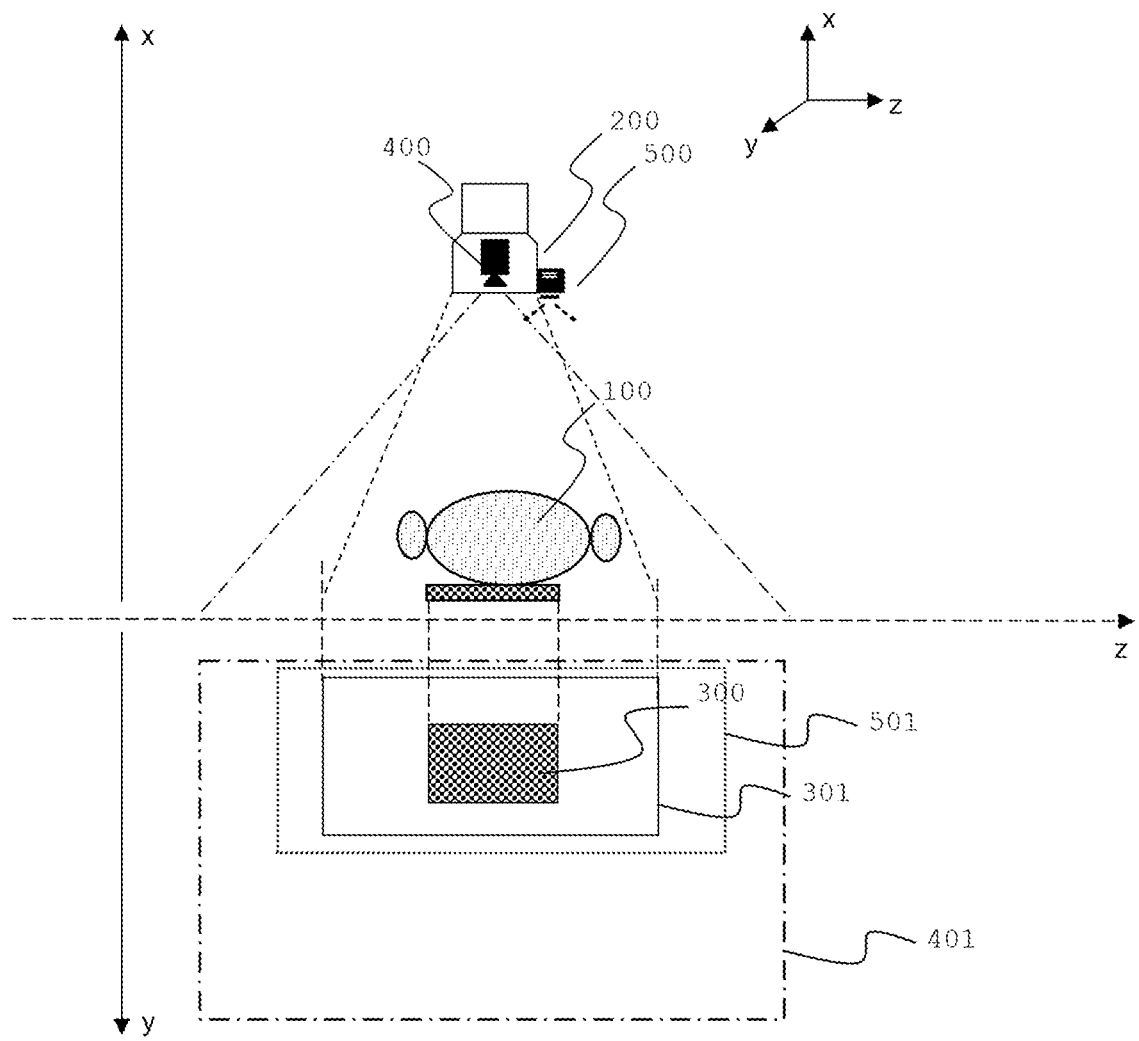

FIG. 6 depicts the same situation as in FIG. 5, but additionally shows a digital image projector (500) that is also attached to or physically associated with the X-ray source (200) of the tomography X-ray device, and of which the imaging beam is oriented in the same direction as the X-ray beam (and in the same direction as the camera device (400)). The digital image projector (500) can project an image (501) onto the an area that at least partially overlaps with the viewing field (401) of said camera device (400). The digital projector (500) can project an overlay image (501) that is visible to the user of the mobile X-ray tomography device, and that is also (at least partially) visible in the field of view (401) of the camera device.

DETAILED DESCRIPTION OF THE INVENTION

In the following detailed description, reference is made in sufficient detail to the above referenced drawings, allowing those skilled in the art to practice the embodiments explained below.

In a first embodiment of the invention, a 2D or 3D camera is attached to the X-ray source or close to the X-ray source, for instance at the collimator head of the X-ray source. This camera is oriented in the same direction as the X-ray beam and captures a viewing field (401) that exceeds the projected field size of the X-ray beam (301), such that a much larger overview is obtained than strictly what would be the exposed field (the projected field size) of the X-ray source. The viewing field can be seen as an area that extends beyond the projected field size of the X-ray beam (301).

The camera may be a conventional 2D color digital camera of which the image can be processed and presented on a computer screen or monitor and that is visible to the operator during the positioning of the mobile X-ray device. The camera may also be a so-called 3D camera providing in addition to the visible view of the extended exposed area also distance information between the visualized patient or object and the camera lens. Since the camera is mounted close to the X-ray source, the depth information provided by the 3D camera also corresponds to the distance between the X-ray source and the object in view of the camera at the concerned pixel-location. In other words, this information may for instance be used to measure the distance to the patient skin (allowing the calculation of the patient thickness), or to measure the distance between the source and the detector (provided that part of it is at least within view of the camera).

As explained above, the viewing field of the camera (401) encompasses the view on the projected field of the X-ray beam (301), such that the camera view (when displayed on a monitor or computer display) oversees the entire positioning scene when positioning the digital imaging detector and patient, while the mobile X-ray device is positioned such that the X-ray tube is in its starting position (199), or at least an estimated starting position. In other words the viewing field of the camera (401) should largely exceed the size of the projected field of the X-ray beam (301) itself. For the application of this invention, the viewing field of the camera (401), should also cover at least a portion of the anticipated collimated projection fields (211, 212, 213) of the X-ray beam during the tomography acquisition path. In other words, the viewing field of the camera (401) should comprise the area where it is expected that the collimated projection fields (211, 212, 213) of the X-ray beam will cast the radiation during the consecutive acquisitions. This implies that the width and height of the viewing field of the camera (401) should be preferably be 2 or 3 times the size of the projected field of the X-ray beam.

The tomographic movement path or trajectory can be divided into at least three trajectory portions (201, 202, 203), called a first, second and third trajectory portion. The first trajectory portion (201) represents the part of the trajectory that the X-ray tube travels during the acceleration or ramp-up of the X-ray tube at position (199) from standstill until it achieves a constant velocity at position (211'). This trajectory portion is not used for acquiring any images as they would not meet the requirements for the tomosynthesis reconstruction, and thus no X-rays are produced by the X-ray tube at this time. The length of this first trajectory portion (201) is determined by the accelerating power of the cart of the mobile X-ray device (or by the accelerating power of the involved telescopic parts of the tube crane), the total weight of the mobile X-ray device and the characteristics of the floor surface on which the cart moves. The length of this trajectory (from standstill until constant velocity) is predictable for a certain mobile X-ray device type and can be measured upfront.

Ideally, and in a preferred embodiment, would the collimated projection field (211) at an X-ray tube position (211'), the position where the X-ray tube reaches its constant velocity, just start to overlap fully with the surface of the digital imaging detector (300). In this case, the mobile X-ray modality would have been positioned in the optimal starting position to ensure that as soon as the X-ray tube reaches its constant velocity, the X-ray exposure would (given the collimator settings and the digital imaging detector's position) fully expose the digital imaging detector.

The second trajectory portion (202) represents the part of the tomography acquisition trajectory during which the X-ray tube moves at a constant velocity, and during which different consecutive tomography acquisitions are captured. The second trajectory portion is also called the acquisition phase. It is during this acquisition phase (202) that the digital imaging detector (300) will continuously capture images at a constant acquisition frequency. The combination of the constant acquisition frequency and the constant velocity of the X-ray source, ensures that the sequence of tomographic images in the interval (202) are captured at the same distance from each other.

The length of the acquisition phase, or the time during which the velocity is kept constant and during which the sequence of tomographic images at a constant time interval may be determined by the amount of overshoot of the beam, meaning that the acquisition phase may continue for as long as the entire detector surface is irradiated. The length of the acquisition phase therefore has to be selected as a programmable parameter in the system by the operator before starting the acquisition sequence. The length of the acquisition trajectory during the acquisition phase (202) determines the depth resolution of the reconstructed image result. The length of the acquisition phase therefore is known ahead of the initiation of the acquisition sequence.

The third trajectory portion (203) represents the part of the tomography acquisition trajectory during which the X-ray tube slows down from an X-ray tube position (213') to a standstill. This length of this trajectory portion is determined amongst others by the braking power of the mobile X-ray cart and the characteristics of the floor surface. The length of this trajectory portion therefore is predictable for a certain system and can be calculated based on the initial speed from which it needs to slow down.

From the above, it is clear that the lengths of the above mentioned trajectory portions can be calculated, given that the required parameters are provided by the operator. Before the acquisition sequence is started, the operator can for instance enter the desired width of the tomosynthesis output image, which will have an impact on the length of the acquisition trajectory.

Based on the information above, it is now possible to calculate the length and direction of the acquisition trajectory for a given starting position and orientation of the cart. Since in the invention a significant portion of the anticipated acquisition trajectory is in view of the 2D or 3D camera, it is possible to indicate or visualize this anticipated acquisition trajectory by marking the digital image with lines, symbols or markings before presenting it to the operator. The position of these lines, markings and symbols on the camera image can be calculated to reflect a physical zone in the field of view of the camera since the camera device is positioned in a fixed physical relationship with the X-ray source and maintains the same perspective as the X-ray source during the tomographic sequence. In other words and as an example, the collimated area of a projected X-ray beam maintains the same shape and size, even when the X-ray source is moved to a different position as long as the movement is parallel to the digital imaging detector.

The real shape or size of the collimated area of the projected X-ray beam onto the object (or patient) surface in the acquired 2D or 3D image will vary with the distance between the object surface and the camera/X-ray source position. The farther the X-ray source (and the camera) is positioned from the body surface, the smaller the sizes and distances on this surface will appear. Therefore in order to calculate the visualization of the acquisition trajectory correctly, this distance has to be taken into account.

Therefore, it will be required to integrate the distance between the body surface and the X-ray source into the calculation of the size of the visualizations in order to be able to correctly overlay the visualizations over the image.

The distance between the X-ray source (or camera) and the body surface may be entered by an operator into the system, or may be obtained through measurements (e.g. from the 3D camera, or another distance measuring device)

In another example, it is possible to mark or delineate zones in the camera image that play an important role in the tomographic acquisition sequence. For example, the exposed area of the acquisition phase that would be applied in case that the mobile X-ray device would use the current position as a starting point, may be visualized on the acquired camera image. Providing the positional information of the exposed area during the acquisition phase in a visual way to the operator at the time of positioning the mobile X-ray device, allows him to adjust the starting position of the cart when needed. This is important, as it is essential that the exposed area during the acquisition phase fully exposes the surface of the digital imaging detector and covers the region of interest for the acquisition. The operator may thus adjust the starting position of the cart when he observes that the marked zone in the camera image does not align correctly with the position of the digital imaging detector behind the patient.

Alternatively, and in yet another embodiment, the acquisition trajectory is adjusted by extending the ramp-up phase of the acquisition trajectory rather than to adjusting the initial starting position said mobile X-ray device. In a case where the position of the mobile X-ray device would require that it should be moved towards the object to achieve the desired initial starting position, it would also be possible to include this additional movement into the (automated) acquisition trajectory itself, such that another manipulation by an operator could be avoided. So, in this case, the acquisition trajectory would not be adjusted interactively by said operator by moving said mobile X-ray device, but rather by extending the ramp-up phase of the acquisition trajectory of the mobile X-ray device.

In a case that the cart position is adjusted, the captured image by the 2D or 3D camera will also change. Based on the altered position of the cart, the lines, markings or symbols will have to be updated according to the change in position and the newly calculated anticipated acquisition trajectory.

In one embodiment can the zone in the camera image representing the exposed area be marked by a color overlay, or as a contour (or a contour line) that may or may not be colored. Other symbols or markings may be envisaged that could provide the desired visual support to the operator in determining the location of objects or areas in the field of view of the camera.

In this embodiment of the invention, and after the marking of the desired region of interest on the captured image is completed, the system calculates the acquisition trajectory, based on the assumption that the current mobile X-ray device position would be used as a starting position (and the selected length of the acquisition phase). The marked region of interest is now superimposed with the markings of the calculated acquisition trajectory, which allows the operator to evaluate whether or not the desired region of interest overlaps with the acquisition trajectory (as calculated from the current mobile X-ray device position). The operator can then, based on this information, adjust the position of the mobile X-ray cart to make it assume an adjusted starting position to ensure a correct acquisition trajectory.

In another embodiment of the invention, the desired or optimum region of interest for capturing the tomosynthesis image is indicated, drawn or marked by the operator on the captured image by the 2D or 3D camera. The operator indicates the desired region of interest by for instance inputting a target contour around the region of interest, or by drawing a contour on the captured image of the 2D or 3D camera by means of an input device. Other methods and means of indicating the desired region of interest on said captured image may be applied such as for instance painting an area by means of a computer mouse, or by a drawing tablet, or by drawing lines on said captured image indicating the boundaries of said desired region of interest.

Based on the position of the drawn contour of the region of interest on the camera image, it is now possible to calculate the needed adjustment of the initial starting position of the mobile X-ray device to ensure that the region of interest will align with the acquisition trajectory when applying this calculated (adjusted) initial starting position. The adjusted initial starting position can now be applied to the mobile X-ray device by driving it in an automated way, or by means of giving the appropriate directions to the operator.

Another important aspect is that the region of interest should overlap in the captured 2 or 3D image with the surface of the digital imaging detector, such that the digital imaging detector should be in view of the collimated projection field (211) of the X-ray source during the acquisition phase. In another embodiment, the system can give guidance to the operator to ensure that the entire surface of the detector is exposed during the acquisition sequence. This guidance can be calculated and given provided that the location of the digital imaging detector is accurately known.

In another embodiment, it is possible to use the 2D and 3D camera data to accurately record the changes in the relative positions of the X-ray source and digital imaging detector during the acquisition sequence. For each acquired image, a corresponding 2D, preferably 3D image, can be recorded and used to reconstruct accurately the relative positions between source and detector. 3D camera reliably record distance data between the camera and the objects within view, which can be recalculated into relative position changes between subsequent image captures.

Based on this information, any physical disturbances (like bumps, deviations, vibrations, . . . ) during the acquisition trajectory may be accounted for by the reconstruction algorithm when using the above relative position data as positional input for the calculation.

In another embodiment, an image analyzer module replaces the operator during his evaluation of the alignment of the calculated acquisition trajectory portion and the intended region of interest of the examination (or the location of the detector behind the patient). This image analyzer module is used to evaluate whether—for instance—the trajectory portion during the acquisition phase coincides with the correct targeted region of interest of the patient. The image analyzer module is thus designed to detect, identify and locate a region of interest. The image analyzer module could be based on a neural network that is trained on detecting specific body parts (such as for instance a chest, a pelvis, a hand, or alike) in a 2D/3D image and locate its position, but may be based on other types of body part detection systems known in the art.

The application of such an image analyzer module in the invention would allow the system to calculate a deviation between the location of the intended region of interest by detecting the location of the body part in the 2D/3D camera image, and the location of the calculated trajectory portion (of e.g. the acquisition phase), such that the location of the initial starting position of the mobile X-ray device can be adjusted automatically, i.e. without the intervention of an operator. This would result in a fully automated selection of the initial starting position for the digital tomosynthesis acquisition.

The invention claimed is:
1. A method for adjusting an initial starting position (199) of an acquisition trajectory (201+202+203) of a mobile X-ray device (220) to perform a portable X-ray tomography acquisition sequence on a region of interest of an object (100), comprising the steps of:
 positioning said mobile X-ray device at said initial starting position (199) such that an estimated acquisition trajectory is aligned with a digital imaging detector (300) by an operator,
 receiving X-ray source collimator settings, and
 calculating said acquisition trajectory of said mobile X-ray device (220) during said portable X-ray tomography acquisition sequence for said initial starting position,
 characterized in that,
 the acquisition trajectory of said mobile X-ray device during said portable X-ray tomography acquisition sequence for said initial starting position is visualized for each change in position of said mobile X-ray device, and said initial starting position for said acquisition trajectory is adjusted interactively by said operator by moving said mobile X-ray device, such that a trajectory portion of said visualized acquisition trajectory is aligned with said region of interest of said patient.

2. The method according to claim 1, wherein a source-to-object distance is received, and wherein the acquisition trajectory of said mobile X-ray device during said portable X-ray tomography acquisition sequence for said initial starting position is visualized and adjusted for said source-to-object distance for each change in position of said mobile X-ray device.

3. The method according to claim 2, wherein the trajectory portion of said acquisition trajectory of said mobile X-ray device during said portable X-ray tomography acquisition sequence for said initial starting position is visualized by projecting a representation of said trajectory portion (301) on said object (100) by a projection device (400) that is physically associated with an X-ray source (200) of said mobile X-ray device.

4. The method according to claim 2, wherein the trajectory portion of said acquisition trajectory of said mobile X-ray device during said portable X-ray tomography acquisition sequence for said initial starting position is visualized by drawing a representation of said trajectory portion on a digital image that is acquired by a camera that is physically associated with an X-ray source of said mobile X-ray device.

5. The method according to claim 4, wherein the digital image that is acquired by said camera is displayed on a display device.

6. The method according to claim 2, wherein said trajectory portion is a constant velocity portion or acquisition phase of said acquisition trajectory.

7. The method according to claim 2, wherein said X-ray source collimator settings are received form an input device from an operator/digitally from the modality.

8. The method according to claim 1, wherein the trajectory portion of said acquisition trajectory of said mobile X-ray device during said portable X-ray tomography acquisition sequence for said initial starting position is visualized by projecting a representation of said trajectory portion (301) on said object (100) by a projection device (400) that is physically associated with an X-ray source (200) of said mobile X-ray device.

9. The method according to claim 1, wherein the trajectory portion of said acquisition trajectory of said mobile X-ray device during said portable X-ray tomography acquisition sequence for said initial starting position is visualized by drawing a representation of said trajectory portion on a digital image that is acquired by a camera that is physically associated with an X-ray source of said mobile X-ray device.

10. The method according to claim 9, wherein the digital image that is acquired by said camera is displayed on a display device.

11. The method according to claim 1, wherein the visualization of said acquisition trajectory is embodied as a color overlay, a contour, a contour line that either is colored or not.

12. The method according to claim 1, wherein said initial starting position is adjusted by an operator by inputting a target contour around said region of interest of said object on said digital image that is displayed on said display device, and wherein said input is used to calculate an adjusted initial starting position for said mobile X-ray device, such that said target contour aligns with said trajectory portion.

13. The method according to claim 12, wherein said mobile X-ray device moves automatically to said adjusted initial starting position.

14. The method according to claim 1, wherein the acquisition trajectory is adjusted by extending the ramp-up phase of the acquisition trajectory rather than to adjusting the initial starting position said mobile X-ray device.

15. The method according to claim 1, wherein said initial starting position for said acquisition trajectory is adjusted automatically by moving said mobile X-ray device based on calculating a deviation between a location of said region of interest of said patient that is determined by an image analyzer module, and a trajectory portion of said calculated acquisition trajectory for said initial starting position.

* * * * *